United States Patent

Hsi et al.

[11] Patent Number: 5,382,666
[45] Date of Patent: Jan. 17, 1995

[54] HETEROCYCLIC INTERMEDIATES

[75] Inventors: Jeffrey D. Hsi, Flemington; William V. Murray, Belle Mead, both of N.J.

[73] Assignee: Ortho Pharmaceutical Corporation, Raritan, N.J.

[21] Appl. No.: 139,253

[22] Filed: Oct. 20, 1993

Related U.S. Application Data

[62] Division of Ser. No. 6,093, Jan. 15, 1993, Pat. No. 5,256,658.

[51] Int. Cl.$^6$ ............................................. C07D 265/30
[52] U.S. Cl. ..................................... 544/106; 544/59; 544/229; 544/403; 546/192
[58] Field of Search ......................... 544/106; 546/192

[56] References Cited

U.S. PATENT DOCUMENTS 3,123,643 3/1964 Palopoli et al. ..................... 544/106
5,095,021 3/1992 Zipplies et al. ..................... 546/192

Primary Examiner—Robert W. Ramsuer
Attorney, Agent, or Firm—John W. Harbour

[57] ABSTRACT

Biphenylyl tetrazoles for treating hypertension in mammals of the formula:

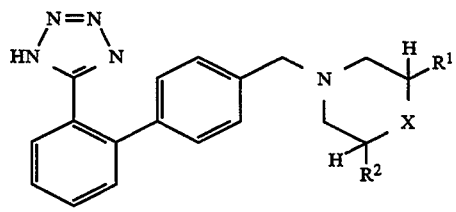

where
  X is $CH_2$, O, S, N—$R^4$, NH, NCHO, $NCOCH_3$ or $NCO_2R^4$;
  $R^1$ and $R^2$ are the same or different and are $C_{1-6}$alkyl; and
  $R^4$ is $C_{1-6}$alkyl;

including methods and intermediates for the production of the same.

5 Claims, No Drawings

HETEROCYCLIC INTERMEDIATES

This is a division of application Ser. No. 08/006,093, filed Jan. 15, 1993, now U.S. Pat. No. 5,256,658.

The present invention relates to angiotensin II inhibitors for the treatment of hypertension. More particularly, the present invention relates to the use of certain tetrazolyl biphenyl compounds for the treatment of hypertension.

BACKGROUND OF THE INVENTION

The renin-angiotensin system (RAS) has an established role in the regulation of blood pressure. To date, effective treatment of hypertension has been achieved through administration of angiotensin converting enzyme (ACE) inhibitors. One such ACE inhibitor is captopril:

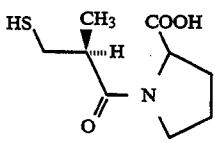

as disclosed in U.S. Pat. No. 4,046,889, Ondetti, M. A., et al., assigned to Squibb. Another such ACE inhibitor is enalapril:

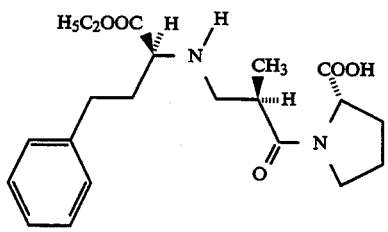

as disclosed in U.S. Pat. No. 4,374,829, Harris, et al., assigned to Merck. Although these ACE inhibitors are widely used, they process undesirable side effects due in part to their mode of action within the RAS.

A more effective treatment might be realized by intervention of the RAS at the angiotensin II receptor level, a more selective point of intervention in the RAS. Angiotensin II receptor antagonists provide a novel approach to the treatment of hypertension.

SUMMARY OF THE INVENTION

The present invention provides angiotensin II receptor antagonists of the general structure (I):

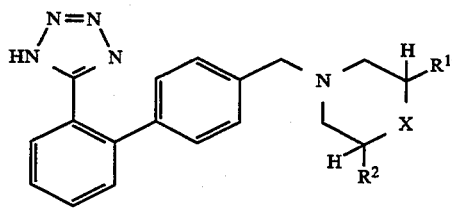

where

X is $CH_2$, O, S, $N-R^4$, NH, NCHO, $NCOCH_3$ or $NCO_2R^4$;

$R^1$ and $R^2$ are the same or different and are $C_{1-6}$alkyl; and $R^4$ is $C_{1-6}$alkyl;

including the pharmaceutically acceptable salts thereof.

The invention also provides novel intermediates of the general structure:

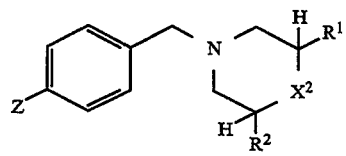

where $X^2$ is $CH_2$, O, S, $N-R^4$ or $N-Si(R^5)(R^6)(R^7)$;

$R^1$ and $R^2$ are the same of different and are $C_{1-6}$alkyl;

$R^4$ is $C_{1-6}$alkyl;

$R^5$, $R^6$, and $R^7$ are the same or different and are methyl, ethyl, t-butyl, or phenyl; and Z is selected from the group consisting of Li, MgCl, MgBr and MgI.

Also provided is a novel process to produce compounds of formula I:

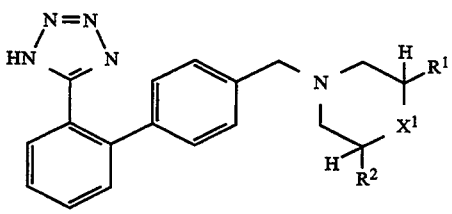

where $X^1$ is $CH_2$, O, S, $N-R^4$ or NH;

$R^1$ and $R^2$ are the same or different and are $C_{1-6}$alkyl; and $R^4$ is $C_{1-6}$alkyl;

which comprises the steps:

(a) coupling an organometallic compound of the formula:

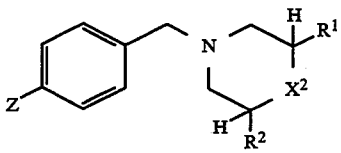

wherein $X^2$ is $CH_2$, O, S, $N-R^4$ or $N-Si(R^5)(R^6)(R^7)$;

$R^1$ and $R^2$ are the same or different and are $C_{1-6}$alkyl;

$R^4$ is $C_{1-6}$alkyl;

$R^5$, $R^6$, and $R^7$ are the same or different and are methyl, ethyl, t-butyl, or phenyl; and Z is selected from the group consisting of Li, MgCl, MgBr and MgI; and an oxazolinyl starting material of the formula:

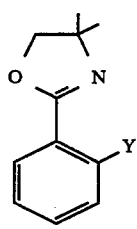

wherein
Y is OMe or F;
to produce an oxazolinyl intermediate of the formula:

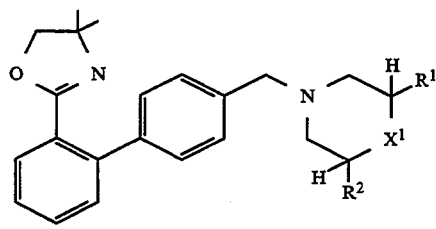

wherein $R^1$, $R^2$ and $X^1$ are defined above;
(b) converting the oxazolinyl moiety of said oxazolinyl intermediate to cyano by treatment with phosphorus oxychloride to produce a cyano compound;
(c) treating said cyano compound with sodium azide and tributylin chloride; and
(d) where $X^2$ is $N—Si(R^5)(R^6)(R^7)$, deprotecting.

Also provided herein are intermediates of the formula:

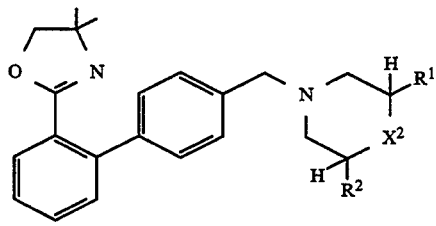

wherein
$X^2$ is $CH_2$, O, S, $N—R^4$, $N—Si(R^5)(R^6)(R^7)$;
$R^1$ and $R^2$ are the same or different and are $C_{1-6}$alkyl;
$R^4$ is $C_{1-6}$alkyl; and
$R^5$, $R^6$, and $R^7$ are the same or different and are methyl, ethyl, t-butyl, or phenyl.

Further provided are intermediates of the formula:

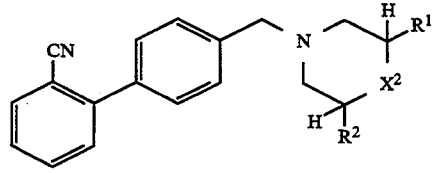

wherein
$X^2$ is $CH_2$, O, S, $N—R^4$, $N—Si(R^5)(R^6)(R^7)$;
$R^1$ and $R^2$ are the same or different and are $C_{1-6}$alkyl;
$R^4$ is $C_{1-6}$alkyl, and
$R^5$, $R^6$, $R^7$ are the same or different and are methyl, ethyl, t-butyl, or phenyl.

DETAILED DESCRIPTION OF THE INVENTION

Active compounds of the present invention may be produced by appropriately utilizing one of three suggested schemes. As seen therein, the various desired substituents are obtained concurrently with the manufacture of the core ring structure.

Referring to Scheme A, certain compounds of Formula I, i.e., those in which $X^1$ is $CH_2$, O, S, $N-C_{1-6}$alkyl or NH, may be produced by addition of fluorotetrazole A1 and the organometallic compound C3 in which Z is Li or $Z^1$Mg (where $Z^1$ is Cl, Br or I), $X^2$ is $CH_2$, O, S, $N—R^4$ or $N—Si(R^5)(R^6)(R^7)$ (where $R^4$ is $C_{1-6}$alkyl, and $R^5$, $R^6$, and $R^7$ are the same or different and are methyl, ethyl, t-butyl, or phenyl) and $R^1$ and $R^2$ are the same or different and are $C_{1-6}$alkyl. For those C3 in which Z is $Z^1$Mg, the addition is, of course, a Grignard reaction and may be carried out in a solvent, such as, diethyl ether, THF, 1,2-dimethoxyethane or dioxane at from $-78°$ C. to reflux, preferably for about 6 to 24 hours. For those C3 in which Z is Li, the addition is an organolithium addition which may be carried out under conditions similar to those of the Grignard reaction. Protection of the tetrazolyl moiety is optional if a molar excess of the organometallic compound is employed. Following the addition, those compounds in which $X^2$ are $N—Si(R^5)(R^6)(R^7)$ are deprotected to NH.

The fluorotetazole A1 may be prepared by techniques well known in the art, such as, those described in Herbst, R. M., and Wilson, K. R., J. Org. Chem. 1957, 22, 1142. The preparation generally comprises reacting 2-fluoro benzonitrile with $NaN_3$ and glacial acetic acid in a solvent, such as, n-butanol. The preparation of the organometallic compound C3 is discussed below.

SCHEME A

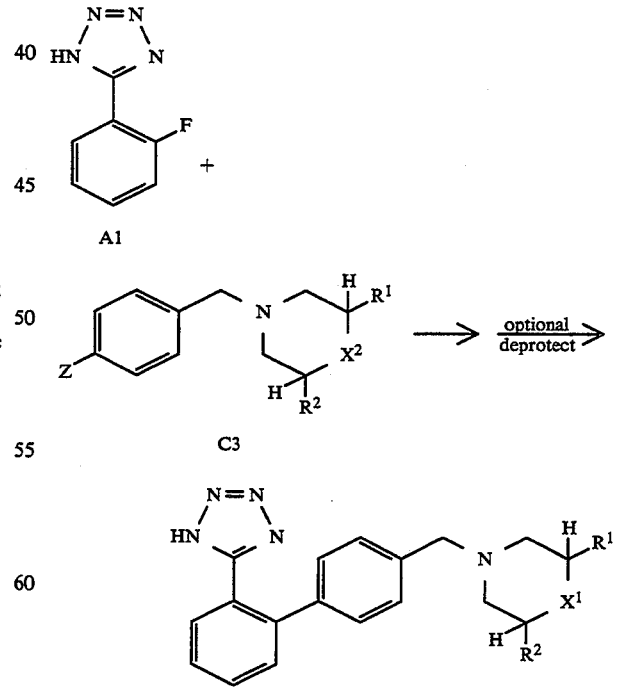

Referring to Scheme B, certain compounds of Formula I, i.e., those in which $X^1$ is $CH_2$, O, S, $N-C_{1-6}$alkyl or NH, may be produced by a direct displacement reaction between tetrzolyl biphenyl compound B1 and heterocycle B2. The direct displacement reaction is carried out by simply refluxing the two reactants in a suitable solvent, such as, $CH_3CN$, with a base, such as, $K_2CO_3$, and, subsequently, deprotecting the tetrazolyl to the desired product in aq. HCl and THF. Following the direct displacement, those compounds in which $X^2$ are $N-Si(R^5)(R^6)(R^7)$ are deprotected to NH.

The tetrazolyl biphenyl B1, may be prepared by known methods, such as, a modification of the method disclosed in U.S. patent application Ser. No. 786,666 filed Nov. 1, 1992, to Russell, et al., hereby incorporated by reference, where B1 might be obtained from the simple bromination of the protected p-tolylphenyl tetrazole. Simply, fluorotetrazole A1 is added in a Grignard reaction with a $p-Z^1Mg$-toluene where $Z^1$ is bromo, chloro or iodo. Protection of the tetrazolyl moiety is optional if a molar excess of the organometallic compound is employed. Protection of the biphenyl tetrazole with an agent, such as, triphenyl methyl chloride and subsequent bromination affords B1.

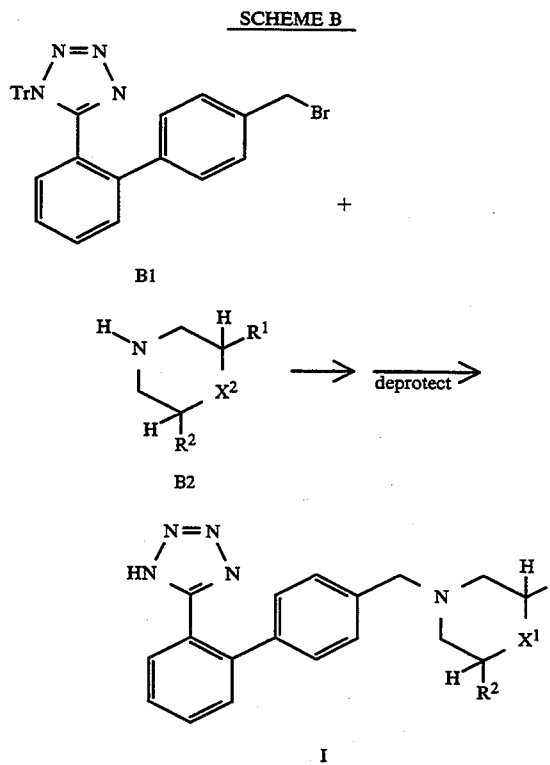

SCHEME B

Referring to Scheme C, organometallic compound C3 is produced by the addition of an activated benzyl compound C1 to heterocycle C2 by alkylation. The alkylation might be carried out in a suitable solvent, such as, $CH_3CN$, DMF or THF with a base, such as, $K_2CO_3$, NaH or KH at temperatures from 0° C. to reflux. The benzyl compound C1, wherein $L^1$ is bromo, chloro or iodo, is activated with a leaving group, L, wherein L is bromo, chloro, iodo, O-mesylate or O-tosylate, by methods well known in the art. The $L^1$ substituent on the alkylation product is subsequently converted to the organometallic moiety, Z, by one of two reactions. In the first reaction, $L^1$ is converted to Z as Li in a lithium-halogen exchange. The lithium-halogen exchange is performed by treatment of the alkylation product with an alkyllithium reagent, such as, n-butyllithium, s-butyllithium or t-butyllithium in an ethereal solvent, such as, THF or diethyl ether. In the second reaction, $L^1$ is converted to Z and MgCl, MgBr or MgI in a Grignard preparation reaction. In the Grignard preparation reaction, the alkylation product is reacted with magnesium turnings in an ethereal solvent, such as, THF or diethyl ether, with or without the presence of an activating reagent, such as, $I_2$ or ethylene dibromide.

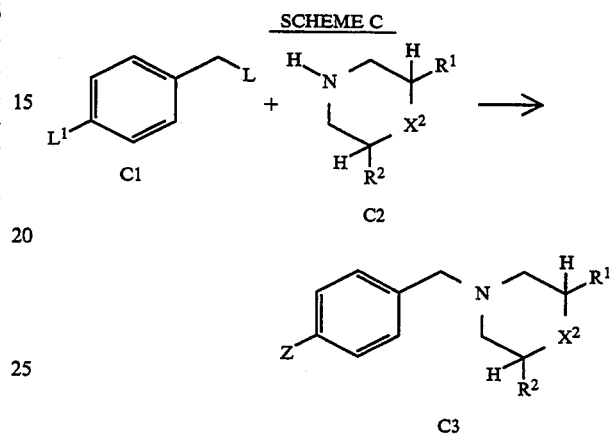

Referring to Scheme D, the biphenylyl oxazoline intermediate D2 is produced by the addition of an organometallic compound C3, wherein $R^1$, $R^2$, $X^2$ and Z are defined above, to o-substituted phenyl oxazoline D1, wherein Y is OMe or F. The addition may be accomplished by one of two well known reactions. For those C3 in which Z is Mg Cl, MgBr or MgI, the addition is, of course, a Grignard reaction and may be carried out in a solvent, such as, diethyl ether, THF, 1,2-dimethoxyethane or dioxane at from −78° C. to reflux, preferably for about 6 to 24 hours. For those C3 in which Z is Li, the addition is an organolithium addition which may carried out under conditions similar to those of the Grignard reaction. Both the Grignard addition and the organolithium addition will function regardless of whether Y is OMe or F. However, Y as F is preferred to obtain higher yields. Subsequently, biphenylyl nitrile D3 is obtained by treatment of D2 with phosphorous oxychloride in pyridine at 0° C. to room temperature. In a last step, target compounds of formula (I) are obtained by treating biphenylyl nitrile D3 with sodium azide and tributyltin chloride in xylene. Following the addition, those compounds in which $X^2$ are $N-Si(R^5)(R^6)(R^7)$ are deprotected to NH.

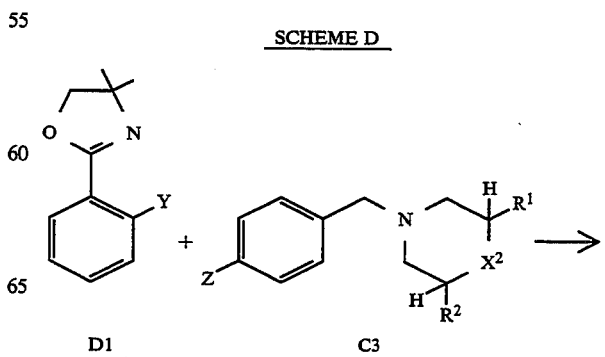

SCHEME D

-continued
SCHEME D

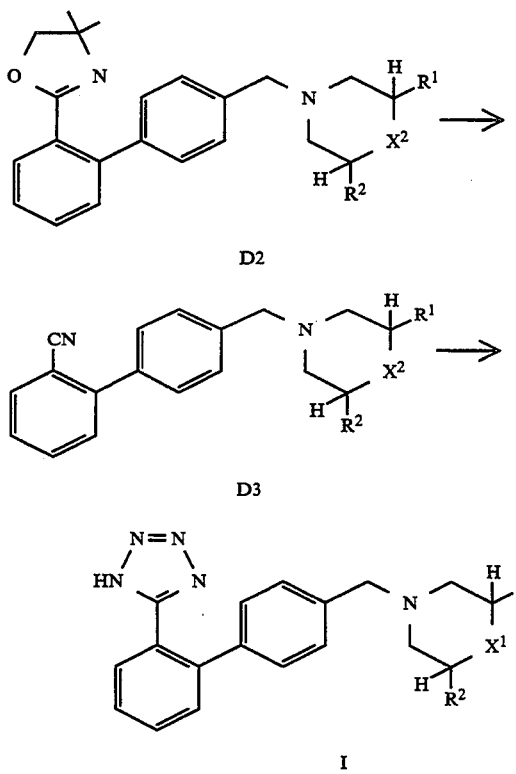

Each of Schemes A, B, and D produce compounds of Formula (I) wherein $X^1$ replaces X. More specifically, those procedures illustrated in Schemes A, B, and D may not be effective to produce those compounds in which X is NCHO, NCOCH$_3$ or NCO$_2$R$^4$ (where R$^4$ is C$_{1-6}$alkyl), i.e. those in which X contains a carbonyl or carboxy. It is not surprising to those skilled in the art that the reason for this is that Schemes A, B, and D contain reaction steps that will degrade X containing carbonyl or carboxy substitution. Thus, compounds containing these X may not be produced or may not be obtained in high yield.

In view of the instability of these substituents to the conditions for making the core ring structure, it is recommended herein that compounds in which X is NCHO, NCOCH$_3$ or NCO$_2$R$^4$ (wherein R$^4$ is C$_{1-6}$alkyl) be derived from a precursor compound of Formula (I) in which X is NH. Broadly, producing these compounds is a two step process in which, as a first step, any of Schemes A, B, or D may be employed to produce the precursor compound in which X is NH and, subsequently, the precursor compound is acylated to the desired X. To produce X as NCHO, the acylating agent is dimethylformamide in the presence of a base, such as NaH or KH, and the solvent may be dimethylformamide itself or there may be additionally added an ethereal solvent. To produce X as NCOCH$_3$, the acylating agent is acetyl chloride and the solvent might be pyridine or dichloromethane. To produce X as NCO$_2$R$^4$, the acylating agent is R$^4$-chloroformate and the solvent is pyridine or dichloromethane.

The pharmaceutically acceptable salts referred to above generally take the form of a salt with tetrazole, where tetrazole is associated with a metal or ammonium cation or tetrazole is reacted with an inorganic or organic acid to form an acid addition salt. Further pharmaceutically acceptable acid addition salts may be formed where, in addition to the nitrogen of tetrazole, a nitrogen of the 6-membered heterocycle is protonated with an inorganic or organic acid. Suitable metal or ammonium cations include sodium, potassium, calcium, magnesium, zinc, ammonium, or alkylammonium, where alkylammonium includes, tetramethylammonium, tetrabutylammonium, choline, triethylhydroammonium, meglumine, triethanolhydroammonium, etc. Suitable salts derived from organic or inorganic acids are the following: acetate, adipate, alginate, aspartate, benzoate, benzenesulfonate, bisulfate, butyrate, citrate, camphorate, camphorsulfonate, cyclopentanepropionate, digluconate, dodecyllsulfate, ethanesulfonate, fumarate, glucoheptanoate, glycerophosphate, hemisulfate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, and undecanoate.

The compounds described above are angiotensin II antagonists as demonstrated by their behavior in aortic rings and the salt depleted rat. The compound of general structure (I) produced in the examples below, i.e., the compound in which X is O and R$^1$ and R$^2$ are cis-dimethyl, displays a pA2 of 6.91, as determined by test procedure 1, below, and good oral activity with a maximum mean arterial pressure drop of 31 mm Hg and duration of 12 hours in the spontaneously hypertensive rat, as determined in test procedure 2, below. These compounds are useful as agents for the treatment of hypertension (lowering high blood pressure), congestive heart failure, elevated ocular pressure, cerebral stroke, angina, cardiac insufficiency, myocardial infarction, and/or diabetic nephropathy. The processes claimed are novel and expedient methods for the synthesis of the claimed compounds.

Pharmaceutical compositions comprising a compound of the invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed. For example, in the case of oral liquid preparations (such as suspensions, elixirs and solutions), water, glycols, oils, alcohols, flavoring agents, preservatives, coloring agents and the like may be used. In the case of oral solid preparations (such as, for example, powders, capsules and tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may De sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, containing from 0.1 to about 1000 mg/kg, and preferably from about 1 to 200 mg/kg of the active ingredients.

The following experimental examples describe the invention in greater particularity and are intended to be a way of illustrating but not limiting the invention.

Biological Test Procedures

1. Inhibition of Angiotensin II Dose-Response in Rabbit Thoracic Aorta

Purpose: To identify competitive receptor antagonists of an angiotensin II-1 activity, i.e., angiotensin II-induced vasoconstriction in in vitro aortic rings.

Procedure: 1.8 to 2.3 kg New Zealand white rabbits are sacrificed with an intravenous sodium pentobarbital overdose and the thoracic aorta gently dissected free from the aortic root to the level of the diaphragm, into ice cold Krebs bicarbonate buffer. The aorta is gently freed of clots and adventitia and cleanly cut with a scalpel into 5 mm segments. Each ring is suspended from a Gould isotonic force transducer in a tissue bath containing 15 mL oxygenated Krebs bicarbonate buffer regulated at 37 ° C. Initial tension is adjusted to 4.0 g and equilibrated over three 20-min wash periods to achieve a baseline tension of 3.0 g. Graded angiotensin II doses are given cumulatively to achieve a maximal contraction. Three 20-min washes are performed to remove the initial angiotensin II effect. The test compound is then given at a screening concentration of $1.0 \times 10^{-5}$M. After observing any effects of the test compound alone, the angiotensin II cumulative dose-response is then repeated in the presence of the test compound.

Analysis: Angiotensin II vasoconstrictor tension in grams is expressed as a percent of maximal contraction for the before and after test compound angiotensin II dose-responses. Angiotensin II $ED_{50}$ and $ED_{90}$ values are determined from the angiotensin II dose-response curves generated before and after test compound. A percent inhibition of the angiotensin II dose-response is calculated by determining the percent of maximal contraction occurring after the test compound at the concentration that achieved a 90% contraction before antagonist: 90-percent contraction occurring after test compound at the $ED_{90}$ before test compound/90×100=% Inhibition.

Controls: Test compounds are dissolved in DMSO as the vehicle and DMSO alone is tested in two rings as a vehicle control in each screening experiment. In this assay, vehicle alone shows a percent inhibition of 5.2±0.7% (n=23 tests).

| Reference Compounds: | Compound | pA2 (95% C.L.) |
|---|---|---|
| | DuP-753 | 8.95 (8.57–9.33) |
| | Saralasin | 9.86 (9.21–10.51) |

2. Test Procedure for Screening Potential Angiotensin II Receptor Antagonists in Salt-Depleted Normotensive Rats Purpose: This test is designed to detect hypotensive effects of a compound after oral dosing in normotensive animals made renin-dependent by salt depletion.

Method: Male 350–450 g Sprague-Dawley rats are implanted with teflon microcannulae via the middle caudal artery under 20 mg/kg intravenous Brevital® anesthesia and permitted a 4–7 day surgical recovery period. Throughout recovery and testing animals are individually housed unrestrained in standard rat metabolism cages and receive continuous 0.5 ml/h intra-arterial 0.25N saline infusion through a spring-shielded swivelling tether connected to an infusion/blood pressure recording system to maintain arterial cannula patency. Animals are maintained on Low Sodium (0.03%) Purina Rat Chow #5881 throughout the study. After the recovery period animals are given oral 50 mg/kg furosemide (Lasix, Hoechst-Roussel Pharmaceutical) doses on two consecutive days to produce marked diuresis and plasma volume depletion that makes maintenance of normal blood pressure highly dependent on function of the renin-angiotensin-aldosterone system. Three hours after the second furosemide dose, rats are given test compound uniformly suspended in 1% methylcellulose (n=3/dose level) or 1 mL 1% methylcellulose vehicle (n=3) orally by gavage and blood pressure is continuously recorded for 24 h using a Buxco computerized data recording system. Compound-induced changes in blood pressure are compared to concurrent vehicle control blood pressures in order to detect drug effect.

Interpretation: Prior to salt depletion, normotensive rats typically show a plasma renin activity (PRA, ng angiotensin 1/mL plasma/h, RIA) of 0.7. After the salt-depletion protocol PRA values taken 3 h after the furosemide dose have risen to about 7.4. Whereas blood pressure of normotensive rats that have not been salt-depleted does not change in response to treatment with the nonpeptide angiotensin receptor antagonist, DuP-753, salt-depleted animals typically respond with a blood pressure decrease of about 35 mmHg (mean arterial pressure, MAP). PRA is increased by this DuP-753 treatment to about 41.4.

Compounds that decrease blood pressure 10 or more mmHg (MAP) compared to concurrent control after oral dosing are considered active in this test. Maximum possible response is about −35 mmHg. Compounds that are not orally active are retested by giving a solution dose intra-arterially through the blood pressure cannula three hours after a furosemide dose.

Experimental

Proton nuclear magnetic resonance ($^1$H NMR) spectra were recorded on a Bruker AC-300 (300 MHz) spectrometer in $CDCl_3$ unless otherwise indicated. The reported values are expressed in parts per million (ppm) downfield from tetramethylsilane (TMS) which was used as an internal standard. Infrared spectra (IR) were recorded on a Beckman Instruments IR8 spectrophotometer and are expressed in reciprocal centimeters ($cm^{-1}$). Mass spectra were obtained on a Finnigan MAT 8230 Double Focusing high resolution mass spectrometer. Melting points were obtained on a Thomas-Hoover apparatus and are uncorrected.

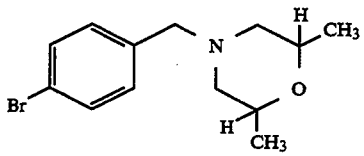

EXAMPLE 1 cis-4-Bromophenylmethyl-2,6-dimethylmorpholine and trans-4-Bromophenylmethyl-2,6-dimethylmorpholine To a solution of 2,6-dimethylmorpholine (12.0 mL, 97.4 mmol) and 4-bromobenzyl bromide (13.5 g, 53.9 mmol) in 200 mL of acetone was added potassium carbonate (40.0 g, 289 mmol) at room temperature. The mixture was heated at reflux for 16 h, then was filtered and the filtrate was concentrated to give a yellow oil. Purification by silica gel flash column chromatography (hexanes:EtOAc; 9:1) gave the cis-dimethylmorpholine (9.87 g, 64%) as a pale yellow solid and the trans-dimethylmorpholine (3.38 g, 22%) as a yellow liquid.

For the cis-isomer: $^1$H NMR (CDCl$_3$): δ1.13 (6H, d, J=6.3 Hz), 1.73 (2H, t, J=10.3 Hz), 2.66 (2H, dt, J=10.3, 1.7 Hz), 3.41 (2H, s), 3.67 (2H, m), 7.20 (2H, d, J=8.4 Hz), 7.44 (2H, d, J=8.4 Hz). MS (DCI): m/z 284 (MH+). mp: 55°-57° C. Anal. Calcd. for C$_{13}$H$_{18}$BrNO: C, 54.94; H, 6.38; N, 4.93. Found: C, 54.92; H, 6.38; N, 4.93.

For the trans-isomer: $^1$H NMR (CDCl$_3$): δ1.22 (6H, d, J=6.5 Hz), 2.12 (2H, dd, J=10.7, 5.7 Hz), 2.44 (2H, dd, J=10.9, 3.1 Hz), 3.33 and 3.41 (2H, ABq, J=13.4 Hz), 4.00 (2H, m), 7.21 (2H, d, J=8.3 Hz), 7.43 (2H, d, J=8.4 Hz). MS (DCI): m/z 284 (MH+). Anal. Calcd. for C$_{13}$H$_{18}$BrNO: C, 54.94; H, 6.38; N, 4.93. Found: C, 45.73; H, 6.43; N, 4.90.

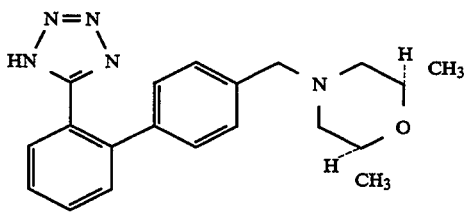

EXAMPLE 2 cis-2,6-Dimethyl-4-[4-(2'-tetrazolophenyl)phenylmethyl]morpholine

To a solution of N-(triphenylmethyl)-5-[4'-(bromomethyl)biphenyl-2-yl]tetrazole (3.36 g, 6.03 mmol) and 2,6-dimethylmorpholine (0.62 g, 5.38 mmol) in 50 mL of CH$_3$CN at room temperature was added sodium bicarbonate (4.50 g, 53.6 mmol). The mixture was heated at reflux for 23 h then was filtered. The filtrate was concentrated to give a yellow oil. Purification of this material by silica gel flash column chromatography (hexanes; EtOAc, 8:2) gave the cis-trityltetrazole (1.675 g, 53%) as a white solid. The trans-trityltetrazole (0.646 g, 20%) was also isolated. To the cis-trityltetrazole (1.598 g, 2.70 mmol) in 8.0 mL of THF was added 3N HCl (4.0 mL) at room temperature. After 43 h at room temperature, the mixture was extracted with Et$_2$O, adjusted to pH 6, then extracted with CH$_2$Cl$_2$. The combined extracts was dried over Na$_2$SO$_4$ and concentrated to give a white solid. Recrystallization from CH$_2$Cl$_2$ gave a solid which was taken up in EtOH and concentrated to give the cis-dimethyl morpholine (0.584 g, 62%), a white powder, as the corresponding hydrochloride salt.

$^1$H NMR (CDCl$_3$): δ1.19 (6H, d, J=6.2 Hz), 2.43 (2H, t, J=11.1 Hz), 3.35 (2H, d, J=11.5 Hz), 4.10 (2H, s), 4.25 (2H, m), 7.10 (2H, d, J=7.9 Hz), 7.40-7.61 (5H, m), 7.82 (1H, d, J=6.4 Hz). MS (DCI): m/z 350 (MH+). mp: 230°-231° C. Anal. Calcd. for C$_{20}$H$_{23}$N$_5$O. HCl.¼ H$_2$O: C, 61.53; H, 6.33; N, 17.94. Found: C, 61.54; H, 6.24; N, 17.90.

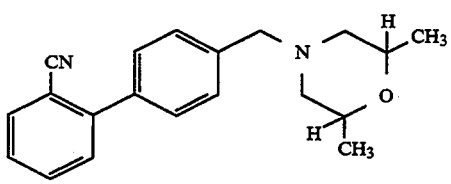

EXAMPLE 3 cis-4-[4-(2'-Cyanophenyl)phenylmethyl]-2,6-dimethylmorpholine and trans-4-[4-(2'-Cyanophenyl)phenylmethyl]-2,6-dimethylmorpholine To a solution of 2,6-dimethylmorpholine (1.90 mL, 15.4 mmol) and 4-(2'-cyanophenyl)phenylmethyl bromide (4.92 g, 18.1 mmol)in 150 mL of CH$_3$CN was added potassium carbonate (7.00 g, 50.6 mmol) at room temperature. The mixture was heated at reflux for 29 h, whereupon it was filtered and the filtrate was concentrated to give a yellow oil. Purification by silica gel flash column chromatography (hexanes:EtOAc; 7:3) gave the cis-dimethylmorpholine (4.36 g, 75%) as a pale yellow solid and the trans-dimethylmorpholine (1.70, 36%) as a pale yellow oil. For the cis-isomer: $^1$H NMR (CDCl$_3$): δ1.16 (6H, d, J=6.3 Hz), 1.80 (2H, t, J=10.7 Hz), 2.75 (2H, d, J=10.8 Hz), 3.54 (2H, s), 3.73 (2H, m), 7.41-7.78 (8H, m). MS (DCI): m/z 307 (MH+). mp: 95°-97° C. Anal. Calcd. for C$_{20}$H$_{22}$N$_2$O: C, 78.40; H, 7.24; N, 9.14. Found: C, 78.54; H, 7.28; N, 9.05.

For the trans-isomer: $^1$H NMR (CDCl$_3$): δ1.26 (6H, d, J=6.5 Hz), 2.19 (2H, dd, J=10.9, 5.7 Hz), 2.51 (2H, dd, J=10.9, 2.8 Hz), 3.46 and 3.53 (2H, ABq, J=13.5 Hz), 4.05 (2H, m), 7.41-7.78 (8H, m). MS (DCI): m/z 307 (MH+).

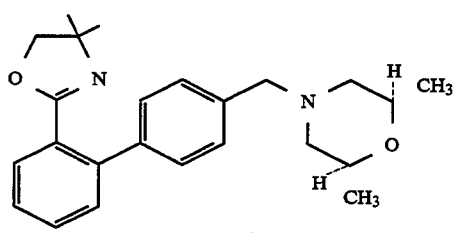

EXAMPLE 4 cis-2,6-Dimethyl-4-[2'-(4,4-dimethyl-2-oxazolinyl)-phenyl]phenyl-methylmorpholine To a solution of cis-4-bromophenylmethyl-2,6-dimethylmorpholine (0.840 g, 2.96 mmol) in 6.0 mL of THF at −78° C. was added 4.00 mL of a 1.3M solution of sec-butyllithium in cyclohexane. The mixture was warmed to −65° C. over 60 min whereupon a solution of 2-(2-fluorophenyl)-4,4-dimethyl-2-oxazoline (0.52 g, 2.69 mmol) in 5.0 mL of THF was added. The mixture was stirred 3.5 h at room temperature then was heated 22 h at reflux. After cooling to room temperature, the mixture was quenched with 10 mL of saturated NaHCO$_3$ solution and was extracted (3×15 mL) with Et$_2$O. The combined extracts were dried over Na$_2$SO$_4$ and concentrated under reduced pressure. Purification by silica gel flash column chromatography (hexanes-:EtOAc, 1:1 to 3:7) gave the biphenyloxazoline (0.683 g, 67%) as a yellow oil. $^1$H NMR (CDCl$_3$): δ1.14 (d, 6H, J=6.3 Hz); 1.27 (s, 6H); 1.76 (t, 2H, J=11.1 Hz); 2.72 (d, 2H, J=10.4 Hz); 3.52 (s, 2H); 3.70 (m, 2H); 3.80 (s, 2H); 7.34 (m, 6H); 7.47 (d, 1H, J=7.2 Hz); 7.70 (d, 1H, J=7.5 Hz). MS (DCl): m/z 379 (MH+). Anal. Calcd. for C$_{24}$H$_{30}$N$_2$O$_2$.¼H$_2$O: C, 75.26; H, 8.03; N, 7.31. Found: C, 75.19; H, 8.03; N, 7.24.

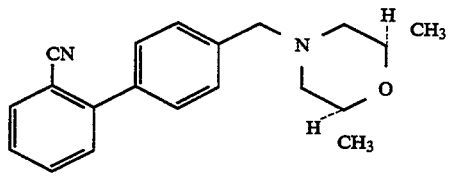

EXAMPLE 5 cis-4-[4-(2'-Cyanophenyl)phenylmethyl]-2,6-dimethylmorpholine

To a solution of cis-2,6-dimethyl-4-[2'-(4,4-dimethyl-2-oxazolinyl)phenyl]-phenylmethylmorpholine (1.302 g, 3.44 mmol) in 6.0 mL of pyridine at 0° C. was slowly added phosphorous oxychloride (0.50 mL, 5.36 mmol). After 15 minutes at room temperature the mixture was heated to 100° C. for 4 hours. The mixture was cooled to room temperature, was quenched with water (20 mL), then was extracted 3×50 mL with EtOAc. The combined extracts were dried over Na$_2$SO$_4$ and concentrated under reduced pressure to give the biphenyl nitrile (0.870 g, 83%) as a tan solid with spectral characteristics identical to those reported above in Example 3.

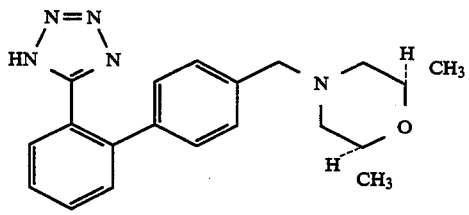

EXAMPLE 6 cis-2,6-Dimethyl-4-[4-(2'-tetrazolophenyl)phenylmethyl]morpholine

To a suspension of cis-4-[4-(2'-cyanophenyl)phenylmethyl]-2,6-dimethylmorpholine (3.973 g, 13.0 mmol) and sodium azide (1.10 g, 16.9 mmol) in 30.0 mL of xylenes at room temperature was added tributyltin chloride (4.40 mL, 17.0 mmol). The mixture was heated at reflux for 45 hours. The mixture was cooled to room temperature, was quenched with 30 mL of 6N HCl, and was exhaustively extracted with EtOAc. The combined extracts were dried over Na$_2$SO$_4$ and concentrated under reduced pressure to give the biphenyl tetrazole dihydrochloride salt (4.420 g, 77%) as a tan solid with spectral characteristics identical to those reported above.

mp: 146°–150° C. Anal. Calcd. for C$_{20}$H$_{23}$N$_5$O.2HCl.½H$_2$O: C, 55.69; H, 6.08; N, 16.24. Found: C, 56.19; H, 5.94; N, 15.81.

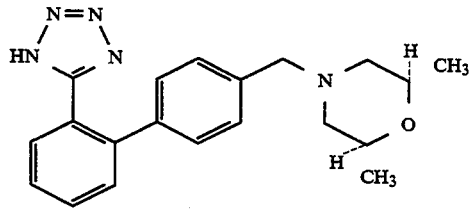

EXAMPLE 7 cis-2,6-Dimethyl-4-[4-(2'-tetrazolophenyl)phenylmethyl]morpholine

To a suspension of magnesium powder (0.310 g, 12.8 mmol) in 10 mL of THF at room temperature was added cis-4-bromophenylmethyl-2,6-dimethylmorpholine (2.78 g, 9.78 mmol). A few drops of dibromoethane and a crystal of I$_2$ was added to initiate the reaction which was allowed to stir for 90 minutes at room temperature. A second flask was charged with 2-(2-fluorophenyl)tetrazole (1.41 g, 8.59 mmol) in 10 mL of THF and a 2.85M solution of methylmagnesium bromide in diethyl ether (3.0 mL, 8.55 mmol) was slowly added. The solution from the first flask was added via cannula under N$_2$ pressure to the second flask at room temperature. The mixture was then heated at reflux for 17 hours. The mixture was cooled and quenched with 6N HCl (3 mL) and the THF was removed under reduced pressure. The resulting aqueous residue was extracted with CH$_2$Cl$_2$ (3×10 mL). The combined extracts were washed with 10% NaOH solution, the base washed acidified with conc. HCl to pH 5 and extracted with CH$_2$Cl$_2$. The CH$_2$Cl$_2$ washes were dried over Na$_2$SO$_4$ and concentrated under reduced pressure to give the crude biphenyl tetrazole (0.380 g, 13%) as a white solid with spectral characteristics identical to those reported above.

What is claimed is:

1. A compound of the general structure:

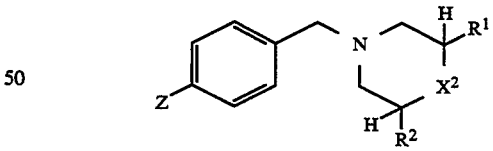

where

X$^2$ is CH$_2$, O, S, N—R$^4$ or N—Si(R$^5$)(R$^6$)(R$^7$);

R$^1$ and R$^2$ are the same or different and are C$_{1\text{-}6}$alkyl;

R$^4$ is C$_{1\text{-}6}$alkyl;

R$^5$, R$^6$, and R$^7$ are the same or different and are methyl, ethyl, t-butyl, or phenyl; and Z is selected from the group consisting of Li, MgCl, MgBr and MgI.

2. A compound of claim 1 wherein Z is Li.

3. A compound of claim 1 wherein Z is MgCl, MgBr and MgI.

4. A compound of claim 1 wherein R$^1$ and R$^2$ are cis-dimethyl and X is

5. A compound of claim 1 wherein R$^1$ and R$^2$ are cis.

* * * * *